United States Patent [19]

Robinson et al.

[11] Patent Number: 5,738,852
[45] Date of Patent: Apr. 14, 1998

[54] METHODS OF ENHANCING ANTIGEN-SPECIFIC T CELL RESPONSES

[75] Inventors: William S. Robinson; Keting Chu, both of Palo Alto, Calif.

[73] Assignee: Solis Therapeutics, Inc., Palo Alto, Calif.

[21] Appl. No.: 663,157

[22] PCT Filed: Apr. 20, 1994

[86] PCT No.: PCT/US94/04367

§ 371 Date: Jul. 29, 1996

§ 102(e) Date: Jul. 29, 1996

[87] PCT Pub. No.: WO94/24267

PCT Pub. Date: Oct. 27, 1994

Related U.S. Application Data

[63] Continuation-in-part of Ser. No. 49,259, Apr. 20, 1993, abandoned.

[51] Int. Cl.⁶ .......................... A61K 39/00; A61K 45/05; A61K 48/00; C12N 15/86
[52] U.S. Cl. .................. 424/199.1; 424/93.2; 424/278.1; 435/320.1; 514/44
[58] Field of Search .......................... 514/44; 435/320.1; 424/278.1, 199.1, 93.2

[56] References Cited

FOREIGN PATENT DOCUMENTS

| WO 88/00971 | 2/1988 | WIPO. |
|---|---|---|
| WO 93/03143 | 2/1993 | WIPO. |
| WO 93/14789 | 8/1993 | WIPO. |
| WO 94/08008 | 4/1994 | WIPO. |
| WO 94/11011 | 5/1994 | WIPO. |
| WO 96/10088 | 4/1996 | WIPO. |
| WO 96/10419 | 4/1996 | WIPO. |
| WO 96/10642 | 4/1996 | WIPO. |
| WO 96/11279 | 4/1996 | WIPO. |
| WO 96/12030 | 4/1996 | WIPO. |

OTHER PUBLICATIONS

Boussiotis et al., 1993, "Activated Human Lumphocytes Express Three CTLA-4 Counterreceptors that Costimulate T-Cell Activation" *Proc. Natl. Acad. Sci. U.S.A.* 90:11059–11063.

Carter, Barrie J., 1992, "Adeno–associated Virus Vectors," *Current Opinion in Biotechnology* 3:533–539.

Cayeux et al., 1995, "Tumor Cell Vaccines Using Cells Contransfected with Cytokine," *2(Suppl).S19*.

Chaux et al., 1996, "T–Cell Co–Stimulation by the CD28 Ligand B7 is Involved in the Immune Response Leading to Rejection of a Spontaneously Regressive Tumor," *Int. J. Cancer* 66:244–248.

Chen et al., 1994, "B7–1/CD80–Transduced Tumor Cells Elicit Better Systemic Immunity than Wild–Type Tumor Cells Admixed with Corynebacterium Parvum," *Cancer Research* 54:5420–5423.

Chen et al., 1992, "Costimulation of Antitumor Immunity by the B7 Counterreceptor for the T Lymphocyte Molecules CD28 and CTLA–4," *Cell* 71:1093–1102.

Chong et al., 1994, "The Use of Combination Gene Therapies for the Treatment of Cancer," *Br. J. Cancer* 71Supp24:13.

Choo et al., 1992, "Indentification of the Major, Parenteral Non–A, Non–B Hepatitis Agent (Hepatitis Agent (Hepatitis C Virus) Using a Recombinant cDNA Approach" *Seminars in Liver Disease* 12:279–288.

Coughlin et al., 1995, "B7–1 and Interleukin 12 Synergistically Induce Effective Antitumor Immunity[1]," *Cancer Research* 55:4980–4987.

DeBenedette et al., 1995, "Role of 4–1BB Ligand in Costimulation of T Lymphocyte Growth and its Upregulation on M12 B Lymohomas by cAMP," *J. Exp. Med.* 181:985–992.

Döhring et al., 1994, "T–Helper–and Accessory–Cell–Independent Cytotoxic Responses to Human Tumor Cells Transfected with a B7 Retroviral Vector," *Int. J. Cancer* 57:754–759.

Eisenberg et al., 1986, "Preliminary Trial of Recombinant Fibroblast Interferon in Chronic Hepatitis B Virus Infection," *Antimicrobial Agents and Chemotherapy* 29:122–126.

Freeman et al., 1989, "B7, a New Member of the Ig Superfamily with Unique Expression on Activated and Neoplastic B Cells," *J. Immunol.* 143:2714–2722.

Freeman et al., 1991, "Structure, Expression, and T cell Costimulatory Activity of the Murine Homologue of the Human B Lymphocyte Activation Antigen B7" *J. Exp. Med.* 174:625–631.

Fujii,Hideki et al., 1996, "Vaccination of Tumor Cells Transfected with the B7–1 (CD80) Gene Induces the Anti–Metastatic Effect and Tumor Immunity in Mice," *Int. J. Cancer* 66:219–224.

Galvin et al., 1992, "Murine B7 Antigen Provides a Sufficient Costimulatory Signal for Antigen–Specific and MHC–Restricted T Cell Activation," *J. Immunol.* 149:3802–3808.

Garcia et al., 1985, "Preliminary Observation of Hepatitis–B Associated Membranous Glomerulonephritis Treated with Leukocyte Interferon," *Hepatology* 5:317–320.

Garcia et al., 1987, "Adenine Arabinoside Monophosphate in Combination with Human Leukocyte Interferon in the Treatment of Chronic Hepatitis," *Int. Med.* 107:278–285.

(List continued on next page.)

*Primary Examiner*—Johnny F. Railey, II
*Attorney, Agent, or Firm*—Pennie & Edmonds LLP

[57] ABSTRACT

Recombinant polynucleotides are provided that confer at least partial immunity on an individual to an infectious intracellular pathogenic agent. The recombinant polynucleotides encode a costimulatory factor and/or a target antigen polypeptide. The immune response that confers the immunity results from the expression of both polypeptides in an antigen presenting cell in the individual. The immunity is to the pathogenic agent that naturally encodes the target antigen polypeptide.

15 Claims, 1 Drawing Sheet

OTHER PUBLICATIONS

Gimmi et al., 1991, "B Cell Surface Antigen B7 Provides a Costimulatory Signal that Induces T Cells to Proliferate and Secrete Interleukin," *Proc. Natl. Acad. Sci. U.S.A.* 88:6575–6579.

Greenberg et al., 1976, "The Effect of Human Leukocyte Interferon on Hepatitis B Virus Infection in Patients with Chronic Active Hepatitis," *New Engl. J. Med.* 295:517–522.

Guilhot et al., 1992, "Hepatitis B Virus (HBV)–Specific Cytotoxic T–Cell Response in Humans: Production of Target Cells by Stable Expression of HBV–Encoded Proteins in Immortalized Human B–Cell Lines," *J. Virol.* 66:2670–2678.

Guinan et al., 1994, "Pivotal Role of the By:CD28 Pathway in Transplantation Tolerance and Tumor Immunity," *Blood* 84(1):3261–3282.

Hafkin et al., 1979, "Effects of Interferon and Adenine Arabinoside Treatment of Hepatitis B Virus Infection on Cellular Immune Responses.," *Antimicrobial Agents and Chemotherapy* 16:781–787.

He et al., 1996, "Costimulatory Protein B7–1 Enhances the Cytotoxic T Cell Response and Antibody Response to Hepatitis B Surface Antigen," *Proc. Natl. Acad. Sci. U.S.A.* 93:7274–7278.

Hinuma et al., 1991, "A Novel Strategy for Converting Recombinant Viral Protein Into High Immunogenic Antigen," *FEBS Lett.* 288:138–142.

Hodge et al., 1995, "Admixture of a Recombinant Vaccinia Virus Containing the Gene for the Costimulatory Molecule B7 and a Recombinant Vaccinia Virus Containing a Tumor–Associated Antigen Gene Results in Enhanced Specific T–Cell Responses and Antitumor Immunity," *Cancer Research* 55:3598–3603.

Hodge et al., 1994, "Induction of Antitumor Immunity by Recombinant Vaccinia Viruses Expressing B7–1 or By–2 Costimulatory Molecules," *Cancer Research* 54:5552–5555.

Hurwitz,A.A. et al., 1995, "The Role of B–7.2 in Anti–Tumor Immunity," *FASEB Journal* 2862:a494.

Jackson et al., 1995, "In vitro Activation of Tumour Specific T–lymphocytes," *Gene Therapy of Cancer 2nd Eur. Conf.* Sep. 7–8, 1995:A9.

Katsanis et al., 1995, "B7–1 Expression Decreases Tumorigenicity and Induces Partial Systemic Immunity to Murine Neuroblastoma Deficient in Major Histocompatibility Complex and Costimulatory Molecules," *Cancer Gene Therapy* 2(1):39–46.

Kirschmeier et al., 1988, "Laboratory Methods. Construction and Characterization of a Retroviral Vector Deomonstrating Efficient Expression of Cloned cDNA Sequences," *DNA* 7:219–225.

Kuchroo et al., 1995, "B7–1 and B7–2 Costimulatory Molecules Activate Differentially the Th1/Th2 Developmental Pathways: Application to Autoimmune Disease Therapy," *Cell* 80:707–718.

Li et al., 1995, "Protective Immunity Induced by B7/CD28–Costimulated γδCells to the EL–4 Lymphoma in Allogenic Athytic Mice" *J. Immunol.* 15:5705–5710.

Li et al., 1994, "Costimulation of Tumor–Reactive CD4 and CD8 T Lymphocytes by B7, a Natural Ligand for CD28, Can be Used to Treat Establised Mouse Melanoma," *J. Immunol.* 153:421–428.

Linsley et al., 1991, "Binding of the B Cell Activation Antigen B7 to CD28 Costimulates T Cell Proliferation and Interleukin 2 mRNA Accumulation," *J. Exp. Med.* 173:721–730.

Matulonis et al., 1995, "Role of B7–1 in Mediating an Immune Response to Myeloid Leukemia Cells," *Blood* 85(9):2507–2515.

McHugh et al., 1995, "Construction, Purification, and Functional Incorporation on Tumor Cells of Glycolipid–Anchored Human B7–1 (CD80)," *Proc. Natl. Sci. U.S.A.* 92:8059–8063.

McLachlin et al., 1990, "Retroviral–Mediated Gene Transfer," *Progress In Nucleic Acid Research and Molecular Biology* 38:91–135.

Modrow et al., 1987, "Computer–Assisted Analysis of Envelope Protein Sequences of Seven Human Immunodeficiency Virus Isolates: Prediction of Antigenic Epitopes in Conserved and Variable Regions," *J. Virol.* 61:570–578.

Montel et al., 1995, "Fas Involvement in Cytotoxicity Mediated by Human NK Cells," *Cellular Immunology* 166:236–246.

Morecki et al., 1995, "Induction of Tumor Immunity by Intact Irradiated Leukemic B Cells (BCL1) Bearing a Tumor–Associated Cell–Surface Idiotype and the Costimulatory B7 Molecule," *Cancer Immunol. Immunother* 41:236–242.

Murphy et al., 1990, "Immunization Against Viruses", *Virology*, Fields, B.N. et al., eds., Raven Press, Ltd., New York, 2nd Edition, Chapter 19, pp. 469–502.

Okamoto et al., 1986, "Nucleotide Sequence of a Cloned Hepatitis B Virus Genome, Subtype ayr Comparison with Genomes of the Other Three Subtypes," *J. Gen. Virol.* 67:2305–2314.

Overell et al., 1989, "Stage–Specific Transformation of Murine B Lineage Cells By ras and myc," *Oncogene* 4:1425–1432.

Overell et al., 1988, "Stably Transmitted Triple–Promoter Retroviral Vectors and Their Use in Transformation of Primary Mammalian Cells," *Mol. Cell. Biol.* 8:1803–1808.

Rao et al., 1996, "IL–12 is an Effective Adjuvant to Recombinant Vaccinia Virus–Based Tumor Vaccines," *Journal of Immunology* 156:3357–3365.

Ratner et al., 1985, "Complete Nucleotide Sequence of the AIDS virus, HTLV–III," *Nature* 313:277–284.

Robinson, 1990, "Hepadnaviridae and Their Replication", *Virology*, Fields, B.N., et al., eds., Raven Press, Ltd., New York, 2nd Edition, Chapter 76, pp. 2137–2169.

Sacks et al., 1982, "Antiviral Treatment of Chronic Hepatitis B Virus Infection: Pharmacokinetics and Side Effects of Interferon and Adenine Arabinoside Alone and in Combination," *Antimicrobial Agents and Chemotherapy* 21:93–100.

Scullard et al., 1982, "Antiviral Treatment of Chronic Hepatitis B Virus Infection: Infectious Virus Cannot be Detected in Patient Serum after Permanent Responses to Treatment.," *Hepatology* 2:39–49.

Scullard et al. 1981, "Antiviral Treatment of Chronic Hepatitis B Virus Infection. I. Changes in Viral Markers with Interferon Combined with Adenine Arabinoside," *J. Inf. Dis.* 143:772–783.

Scullard et al. 1981, "Antiviral Treatment of Chronic Hepatitis B Virus Infection: Improvement in Liver Disease with Interferon and Adenine Arabinoside," *Hepatology* 1:228–232.

Seeger et al., 1984, "Nucleotide Sequence of an Infectious Molecularly Cloned Genome of Ground Squirrel Hepatitis Virus," *J. Virol.* 51:367–375.

Shamash et al., 1995, "Induction of CD80 Expression in Low–Grade B Cell Lymphoma—A Potential Immunotherapeutic Target," *Leukemia* 9:1349–1352.

Smith, C.I., J. Weissberg, P. B. Gregory, W.S. Robinson, L. Bernhardt and T.C. Merigan, 1983, "Acute Dane Particle Suppression with Recombinant Leukocyte A Interferon in Chronic Hepatitis B Virus Infection," *J. Infect. Dis.* 148:907–913.

Smith et al., 1982, "Vidarabine Monophosphate and Human Leukocyte Interferon in Chronic Hepatitis B Infection," *J. Am. Med. Assoc.* 247:2261–2265.

Sulé–Suso et al., 1995, "A B7–1 Transfected Human Melanoma Line Stimulates Proliferation and Cytotoxicity of Autologous and Allogeneic Lymphocytes," *Eur. J. Immunol.* 25:2737–2742.

Towner et al., 1995, "Murine B16F10 Melanoma Cells and the Beneficial Effects of Immune Modulator Gene Transfetion," *J. Cell Biochem. Suppl.* 21A:427.

Townsend et al., 1993, "Tumor Rejection After Direct Costimulation of CD8+ Cells by B7–Transfected Melanoma Cells," *Science* 259:368–370.

Townsend et al., 1994, "Specificity and Longevity of Antitumor Immune Responses Induced by B7–Transfected Tumors," *Cancer Research* 54:6477–6483.

Wang et al., 1996, "Induction of Autologous Tumor Specfic Cytotoxic T–Lymphocyte Activity Against a Human Renal Carcinoma Cell Line by B7–1 (CD80) Costimulation," *Journal of Immunotherapy* 19(1):1–8.

Wendtner et al., 1995, "Recombinant Adeno–Associated Virus (rAAV) Allows Stable and Functional Expression of B7–1 Antigen (CD80) in Human Plasmocytoma Cells," *J. Cell Biochem. Suuppl.* 21A:428.

Westerman et al., 1995, "Tumor Cell Membrane Liposomes with the Addition of The Costimulatory Molecule B7 a an Experimental Tumor Vaccine," *FASEB J.* A514.

Whitton et al., 1990, "Virus–Induced Immune Response Interactions", *Virology*, Fields, B.N. et al., eds., Raven Press, Ltd., New York, 2nd Edition, Chapter 15, pp. 369–381.

Williams et al., 1996, "Constitutive Expression of B7–1 (CD80) on Mouse keratinocytes Does Not Prevent Development of Chemically Induced Skin Papillomas and Carcinomas," *Journal of Immunology* 156:3382–3388.

Yang et al., 1995, "In Vitro Priming of Tumor–Reactive Cytolytic T Lymphocytes by Combining IL–10 with By–CD28 Costimulation," *Journal of Immunology* 155:3897–3903.

Yang et al., 1995, "Antitumor Immunity Elicited by Tumor Cells Transfected with B7–2, a Second Ligand for CD28/CTLA–4 Costimulatory Molecules," *Journal of Immunology* 154:2794–2800.

METHODS OF ENHANCING ANTIGEN-SPECIFIC T CELL RESPONSES

CROSS-REFERENCE TO RELATE APPLICATIONS

The present application is a national phase application under 35 U.S.C. §371 of PCT/US94/04367, filed Apr. 20, 1994, which is a continuation-in-part application of U.S. Ser. No. 08/049,259, filed Apr. 20, 1993, now abandoned, the contents of which are incorporated by reference herein in its entirety.

FIELD OF THE INVENTION

This invention relates to methods of preventing new infections, curing current infections and treating chronic infections caused by intracellular infectious agents. The methods encompass using gene therapy to enhance the interaction between ligands that costimulate T cell activation. More specifically, this invention relates to materials and methods of gene therapy in which genes encoding an antigen from an infectious agent and ligands that costimulate T cell activation are co-expressed in the cells of the host animal to prevent or treat chronic infection. This method stimulates or enhances immune responses To antigens of infectious agents by enhancing the antigen-specific T cell response thus providing protection against new infection or terminating chronic infection.

BACKGROUND OF THE INVENTION

Many infectious agents are capable of causing infection and disease in a host organism; examples of such infectious agents include protozoa, fungi, bacteria, viruses and even worms. Of these infectious agents, those with the mechanism to act intracellularly pose the most significant challenge for prevention and treatment. This is particularly true where the host of the intracellular infectious agent is a mammal, such as man.

Mammals have a complex immune system which has several different mechanisms for defending against an invasion by an infectious agent. Under normal circumstances, the immune system functions to ultimately eliminate the infectious agent from the mammalian host's system. Most infections are self-limiting because the mammalian immune system is generally able to eliminate the infectious agents. Problems arise, however, when the immune system is unable to, or does not, respond to the presence of an infectious agent. In this scenario, infections can become chronic and can persist for many years or even the life-time of the infected human or animal, often resulting in serious disease.

Traditional, standard vaccines expose the immune system to a foreign antigen such as those of infectious agents to elicit an antigen-specific immune response. The immune response is most often humoral and not cellular, that is, it results in production of antibodies but not T cell-based immunity as discussed below. Effective vaccination prevents infection or modifies diseases resulting from infection caused by the infectious agent to which the vaccine is directed.

Immune responses that elicit neutralizing antibodies are sufficient for preventing infections with certain viruses. Murphy et al. (1990). Thus, infection by these viruses can be prevented by vaccination with antigens that elicit neutralizing antibodies. For some viruses and non-virus infectious agents, however, neutralizing antibodies either cannot be elicited or, if elicited, are insufficient to prevent infection and/or disease progression.

Two traditional vaccine types are killed viruses and live attenuated viruses. Killed viruses consist of either whole virions or other infectious agents the infectivity of which has been inactivated. These vaccines may also consist of antigenic subunits or component parts of virions or other infectious agents. These vaccines are administered by parenteral inoculation or exposure to mucous membranes. Live attenuated vaccines consist of live virus or other infectious agents with genetically altered virulence. When used for vaccination, these vaccines cause a reduced form of the disease, or no disease at all.

A third vaccine approach has been investigated and used experimentally but is not yet in clinical use. This approach is the utilization of live agents such as viruses or bacteria as vectors to express vaccine antigens of heterologous infectious agents. A gene or nucleotide sequence encoding the antigen is expressed by the vector and when used in vaccination, exposes the host to the antigen. An immune response to the antigen is expected to protect the host from the infectious agent from which the antigen was derived.

Examples of killed vaccines include tetanus toxoid, influenza virus subunit, rabies, polio and HBV. Examples of live attenuated vaccines include *Salmonella typhi* Ty 21-a and live vaccines for polio, measles, rubella, mumps, smallpox and yellow fever viruses. Examples of live vectors used to express heterologous vaccine antigens include vaccinia virus, adenovirus, adeno-associated virus and *S. typhi* Ty 21-a strain.

Examples of chronic infections associated with significant morbidity and early death include the two human hepatitis viruses, hepatitis B virus (HBV) and hepatitis C virus (HCV) which cause chronic hepatitis, cirrhosis and liver cancer. HBV infection in man closely parallels the infections caused by the closely related hepadnaviruses in certain animals including ground squirrel hepatitis virus (GSHV) which infects the Beechey ground squirrels, woodchuck hepatitis virus (WHV) which infects woodchucks, and duck hepatitis B virus (DHBV) which infects ducks. Robinson, in, *Virology*, 2nd Ed., ed. B. Fields, Raven Press, New York, pp. 2137–2169 (1990).

Additional examples of chronic infections in man caused by viral infectious agents include those caused by the human retroviruses: human immunodeficiency viruses (HIV-1 and HIV-2), which cause acquired immune deficiency syndrome (AIDS); and human T lymphotropic viruses (HTLV-1 and HTLV-2) which cause T cell leukemia and myelopathies. Many other infections such as human herpes viruses including the herpes simplex virus (HSV) types 1 and 2, Epstein Barr virus (EBV), cytomegalovirus (CMV), varicella-zoster virus (VZV) and human herpes virus 6 (HHV-6) are not eradicated by host mechanisms, but rather become chronic and in this state may cause disease. Chronic infection with human papilloma viruses is associated with cervical carcinoma. Numerous other viruses and other infectious agents replicate intracellularly and may become chronic when host defense mechanisms fail to eliminate them. These include pathogenic protozoa (e.g., *Pneumocystis carinii*, Trypanosoma, Leishmania, Malaria and *Toxoplasma gondii*), bacteria (e.g., mycobacteria, salmonella and listeria), and fungi (e.g., candida and aspergillus).

Treatment of chronic virus infections resulting in significant clinical benefit has not been successful largely because such treatments fail to terminate the infection or eliminate the virus. Previous treatments include administration of small chemical compounds such as nucleoside analogs or biologically active proteins such as interferons. These treatments inhibit virus replication but do not eliminate virus from cells or virus infected cells themselves and may result in limited disease improvement only during their administration. Unfortunately, viral infections are often exacerbated when administration of the drug is discontinued.

Common antiviral treatments include nucleoside analogues such as azidothymidine (AZT), dideoxyinosine (DDI) and dideoxycytodine (DDC) for chronic HIV infection and associated AIDS, and adenine arabinoside (araA) for HBV infection and associated liver disease. Interferons similarly suppress HBV and HCV during therapy of chronic infection but the virus usually returns to pretreatment levels and the disease is exacerbated when therapy is discontinued.

One important mechanism employed by the mammalian immune system for controlling and ultimately eliminating ongoing infections by intracellular infectious agents is the activated cellular immune response by activation of certain T cells. T cell activation results in a cytotoxic T lymphocyte (CTL) response directed at viral (or other intracellular infectious agents) antigens on the infected cell surface and elimination of the infected cells. Guilhot et al., *J. Virol.*, 66:2670–2678 (1992). This ultimately results in the elimination of infected cells and the infectious agent within the infected cells. For a general discussion of immune responses to viral infectious agents, see Whitton et al., in, *Virology*, 2nd Ed., ed. B. Fields, Raven Press, New York, pp. 369–381 (1990); and Roitt, Essential Immunology, 7th Ed. (1991).

Activation of T cells occurs when the T cell receptor (TCR) forms a ternary complex with an antigen peptide complexed with a self-MHC (major histocompatibility complex) molecule on the surface of professional antigen-presenting cells (APC). Professional APCs include macrophages and activated B cells. Townsend et al., *Cell*, 44:959–968 (1986); Townsend et al., *Ann. Rev. Immunol.*, 7:601–624 (1989); Bjorkman et al., *Nature*, 329:512–518 (1987); and Jardetsky et al., *Nature*, 353:326–329 (1991). The ternary complex allows for a costimulatory signal to pass between the cells. Activation of T cells requires not only recognition of the antigen peptide-MHC complex by the TCR, but also the interaction of "costimulatory factors," located on the surface of APCs, with specific molecules on the surface of the T cells, the "costimulatory ligand." Freeman et al., *J. Exp. Med.*, 174:625–691 (1991). As used herein, costimulatory factors on APCs include, but are not limited to, the B7-1 protein which specifically binds CD28 and CTL-4 proteins on the surface of T cells and the B7-2 and B7-3 proteins which bind CTLA-4 in T cell activation. Boussiotis et al., *Proc. Natl. Acad. Sci. USA*, 90:11059–11063 (1993). B7 ligands are expressed exclusively by professional APCs. Freeman et al., *J. Exp. Med.*, 174:625–631 (1991); Razi-Wolf et al. (1992); and Larsen et al. (1992). The interaction of CD28 and B7-1 has been shown to be essential for T cell activation. Jenkins et al., *J. Immunol.*, 140:3324–3330 (1988); Linsley et al. (1990); Linsley et al., *J. Exp. Med.*, 173:721–730 (1991); Gimmi et al., *Proc. Natl. Acad. Sci. USA*, 88:6575–6579 (1991); Jenkins et al., *J. Immunol.*, 147:2461–2466 (1991); and Harding et al. (1992).

One of the costimulatory molecules found on the APC is the B7 protein which is the ligand for the T cell surface differentiation antigen CD28. B7 expression, typically effected by professional APCs, has been found to be of critical importance to the activation of naive T cells. Larsen et al., *J. Exp. Med.*, 176:1215–1220 (1992). Other studies have shown that there is a direct relationship between the increase in functional activity of the T cell with the increase in B7 expression. Razi-Wolf et al., *Proc. Natl. Acad. Sci. USA*, 89:4210–4214 (1992). T cells are rendered anergic when they, encounter antigen peptides on cells lacking the costimulatory ligand for which CD28 is a receptor. Harding et al., *Nature*, 356:607–609 (1992).

Viral antigens can be degraded in infected cells when specific viral antigen peptide fragments that bind MHC class I molecules are presented at the cell surface where they serve as targets for MHC restricted CTL. Whitton et al. (1990). However, most infected cells in virally infected hosts are not professional APCs expressing costimulatory proteins. Furthermore, infected cells lacking costimulatory molecules such as B7-1, B7-2, B7-3 may not elicit an effective cellular immune response. When such mechanisms are inadequate and fail to eliminate the agent, infections may persist and become chronic.

Some immunologic mechanisms, such as CTL responses, that are involved in resolving an ongoing infection caused by an intracellular infectious agent, may also play a role in preventing new infections. While other immunologic mechanisms, such as a neutralizing antibody, clearly appear to be more important for preventing certain viral infections than for resolving an ongoing infection. In the case of neutralizing antibodies, antibodies directed against surface antigens can act to neutralize the infectivity of the virus by promoting viral aggregation and ultimately removal of the virus from the bloodstream. Viral infections that are typically blocked by a virus neutralizing antibody, can also be prevented by immunization with antigens that elicit the same neutralizing antibodies. However, for other intracellular infectious agents, a neutralizing antibody cannot be elicited or, when it is elicited, is insufficient for protection. Nonetheless, protection can be conferred by the introduction of an appropriate immunizing agent. In such cases, the cellular immune mechanisms appear to facilitate ability of the immunizing agent to protect against infection. In order for the immune response to result in protection, the immunizing agent must elicit a strong and persistent CTL response. Murphy et al., in, *Virology*, 2nd Ed., ed. B. Fields, Raven Press, New York, pp. 469–502 (1990).

Thus, there has been a need for a method of enhancing the immune response to intracellular infectious agents, such as viruses, by eliciting a strong CTL response. The present invention satisfies that need.

SUMMARY OF THE INVENTION

The present invention provides materials and methods for enhancing the immune response of an individual to an intracellular infectious agent, such as a virus, protozoan, fungus, or bacteria. The materials include vectors encoding a costimulatory factor for T cell activation (hereinafter "costimulatory factor") and a "target antigen" from the infectious agent. The vector, either as a polynucleotide or packaged into a virus assembly, is either directly administered to the individual to be treated, or alternatively, is inserted into a cell which is then administered to the individual to be treated. The administration of the genetic information encoding the costimulatory factor and the target antigen enhances the immune response by, inter alia, eliciting the generation of CTLs directed at cells infected with the infectious agent from which the target antigen is derived.

Accordingly, one embodiment of the invention is a recombinant polynucleotide comprised of a region encoding a costimulatory factor operably linked to a transcriptional control region and further comprised of a region encoding a target antigen polypeptide operably linked to a transcriptional control region. Expression of the costimulatory factor and target antigen polypeptide in an individual confers at least partial immunity in the individual to an intracellular infectious agent that naturally encodes the target antigen polypeptide. The recombinant polynucleotide my be comprised of a viral vector or other vectors as described below.

Another embodiment of the invention is a host cell transformed with a recombinant polynucleotide comprised of a region encoding a costimulatory factor operably linked to a transcriptional control region and with a recombinant polynucleotide comprised of a region encoding a target antigen polypeptide operably linked to a transcriptional control region. Expression of the costimulatory factor and target antigen polypeptide in the individual confers at least partial immunity to an intracellular infectious agent that naturally encodes the target antigen polypeptide.

Still another embodiment of the invention is a method of using a recombinant polynucleotide comprised of a region encoding a costimulatory factor operably linked to a transcriptional control region and with a recombinant polynucleotide comprised of a region encoding a target antigen polypeptide operably linked to a transcriptional control region, the method comprising administering the recombinant polynucleotide to an individual in a therapeutically effective amount; and determining a lessening of a physical symptom associated with a response to infection by an intracellular pathogen that naturally encodes the target antigen.

Yet another embodiment of the invention is a method of using the above-described recombinant polynucleotides comprising transforming a host cell with the polynucleotide. Also claimed are host cells prepared by this method, and progeny thereof.

DETAILED DESCRIPTION OF THE DRAWING

Figure 1:
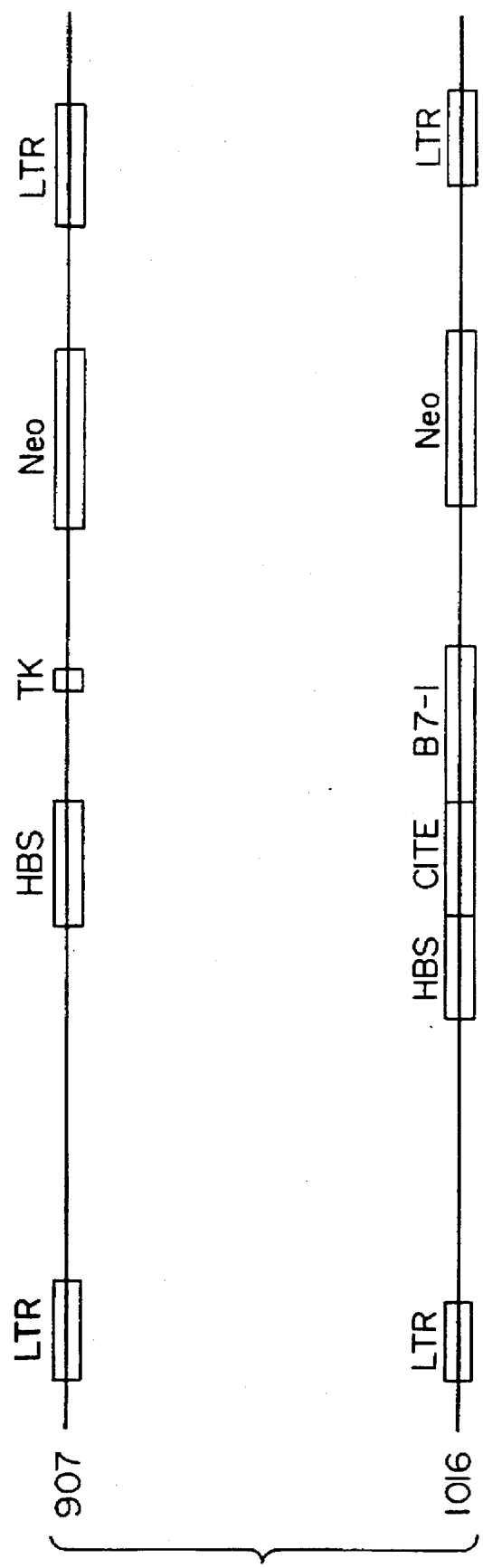
FIG. 1 is a line drawing of two virus vectors.

The critical role of costimulatory factors is to make cells expressing the desired target antigens, such as vital antigens, effective APCs in order to facilitate T cell activation. By creating a system which expresses a costimulatory factor (or a functional portion thereof) concurrently with a target antigen, the resulting response leads to elimination of infected host cells and stronger protection of uninfected hosts cells against new infections.

The invention teaches that immunotherapy that introduces into an individual genetic information encoding the functional portions of a costimulatory factor and a target antigen can be used to activate and/or enhance the immune response of an infected mammalian host. The enhancement includes a cellular response to infections caused by the intracellular infectious agent from which the target antigen is derived, and an induced protective immune response in uninfected cells to prevent new infection to the infectious agent.

The following terms used herein are defined as follows.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

"Treatment" as used herein refers to prophylaxis and/or therapy. The effectiveness of a treatment can be determined by the alleviation of one or more symptom normally associated with a disease caused by an intracellular pathogen.

"Intracellular pathogen" refers to an agent capable of causing a disease state in a susceptible individual, in which part or all of the replicative cycle of the pathogen occurs within the cells of an infected individual. Intracellular pathogens include, for example, protozoa, fungi, bacteria, and viruses.

"Helper cells" or "$T_H$ cells" are a functional subclass of T cells which can help to generate cytotoxic T cells and cooperate with B cells in the production of an antibody response. Helper cells Usually recognize antigen in association with class II MHC molecules.

An "antigen specific T cell clone" is comprised of the progeny of a single cell; the cells in this type of clone are of the same phenotype and are all targeted towards the same antigen. Methods of preparing antigen-specific T cell clones are known in the art.

The term "recombinant expression vector" refers to a replicable unit of DNA or RNA in a form capable of being introduced into a target cell by transformation, electroporation, transduction or Viral infection, and which codes for the expression of a heterologous structural coding sequence, for example, a cytokine, which is transcribed into mRNA and translated into protein under the control of elements having a regulatory role in gene expression. Such vectors will preferably also contain appropriate transcription and translation control sequences, including initiation sequences operably linked to the coding sequence.

"Recombinant," as used herein, means that a particular DNA sequence is the product of various combinations of cloning, restriction, and ligation steps resulting in a construct having a structural coding sequence distinguishable from homologous sequences found in natural systems. Generally, DNA sequences encoding the structural coding sequence, for example cytokines, can be assembled from cDNA fragments and short oligonucleotide linkers, or from a series of oligonucleotides, to provide a synthetic gene which is capable of being expressed in a recombinant transcriptional unit. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present. 5' or 3' from the open reading frame, where such sequences do not interfere with manipulation or expression of the coding regions.

"Recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA Complement as the original parent, due to natural, accidental, or deliberate mutation.

A CTL is "cytolytically specific for" cells expressing antigens if the CTL is capable of selectively recognizing and lysing the cells bearing the antigen. A CTL is "cytolytically reactive against" cells expressing antigens if the CTL is capable of lysing the cells bearing the antigen, without regard to its ability to selectively recognize such cells.

"Antigen specific expression" refers to expression that occurs when the T cell recognizes its cognate antigen.

"Cognate antigen" refers to an antigen, a peptide of which when associated with an MHC molecule forms a ligand that binds to a lymphocyte that recognizes it and causes triggering of signals for the effector function of the cell and/or for proliferation.

"Target antigen" refers to an antigen that when expressed in a cell can elicit a CTL response directed at cells expressing that antigen.

An "agretope" is the portion of an antigen or antigenic fragment which allows it to bind to an MHC molecule.

An "activated lymphocyte" is one that as a result of binding of a cognate antigen peptide:MHC molecule is producing polypeptide stimulatory factors (including, for example, cytokines) at a level that is elevated relative to the lymphocyte without the bound ligand.

A "transcriptional regulatory region" encompasses all the elements necessary for transcription, and may include elements necessary for regulation and cell-specific transcription. Thus, a transcriptional regulatory region includes at least the promoter sequence, and my also include other regulatory sequences such as enhancers, and transcription factor binding sites.

"Operably linked" refers to a juxtaposition wherein the components so described are in a relationship permitting them to function in their intended manner. For instance, a promoter is operably linked to a coding sequence if the promoter affects its transcription or expression.

The term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory Sequences" refer to those sequences normally associated with (for example within 50 kb) of the coding region of a locus which affect the expression of the gene (including transcription of the gene, and translation, splicing, stability, or the like of the messenger RNA). Regulatory sequences include, inter alia, promoters, enhancers, splice sites and polyadenylation sites.

The "sense strand" of a nuclei acid contains the sequence that has sequence homology to that of the cognate mRNA. The "anti-sense strand" contains a sequence which is complementary to that of the "sense strand".

An "individual" as used herein refers to vertebrates, particularly members of the mammalian species, and includes, but is not limited to, domestic animals, sports animals, and primates, including humans.

"Immunization" refers conferring a state of immunity upon an individual by administration of a therapeutic or prophylactic agent.

By "immunity" is meant a lessening and/or prevention of one or more physical symptoms associated with a response to infection by the pathogen from which the target antigen was derived.

An "immune response" to a composition or vaccine is the development in the host of a cellular and/or antibody-mediated immune response to the intracellular infectious agent that encodes the target antigen. Usually, such a response comprises the individual producing CTLs and/or B cells and/or a variety of classes of T cells directed specifically to APCs expressing the target antigen.

A "therapeutically effective amount" of a composition is a dose sufficient to induce an immune response and/or to confer immunity against an intracellular infectious agent that naturally encodes the target antigen.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis; MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos Eds. 1987), HANDBOOK OF EXPERIMENTAL IMMUNOLOGY, (D. M. Weir and C. C. Blackwell, Eds.); CURRENT PROTOCOLS IN MOLECULAR BIOLOGY, (F. M. Ausubel, R. Brent, R. E. Kingston, D. D. Moore, J. G. Siedman, J. A. Smith, and K. Struhl Eds. 1987); and CURRENT PROTOCOLS IN IMMUNOLOGY (J. E. Coligan, A. M. Kruisbeek, D. H. Marguiles, E. M. Shevach and W. Strober Eds. 1991). All patents, patent applications, and publications mentioned herein, both supra and infra, are hereby incorporated herein by reference.

In accordance with the invention, APCs which express a target antigen and are capable of stimulating a T cell response, preferably a CTL response, are created either in vivo or in vitro by the insertion of one or more recombinant polynucleotides containing a sequence encoding at least one costimulatory factor and at least one target antigen polypeptide, such that the costimulatory factor(s) and the target antigen polypeptide(s) are expressed within the recipient host cell.

The costimulatory factor expressed from the recombinant polynucleotide will include at least a portion of the protein sufficient to allow binding of the cell expressing the costimulatory factor to its costimulatory ligand. Methods for determining such binding are known in the art. See, for example, Linsley et al. who describe a procedure wherein the cells to be tested are labeled with $^{51}Cr$ and then incubated with either $CD28^+$ and $CD28^{31}$ CHO cells, and the adhesion of the labelled cells to the CHO cells is determined by $^{51}Cr$ release. Proc. Natl. Acad. Sci. USA, 87:5031–5035 (1990). The extracellular domains and transmembrane domains of the costimulatory factors are usually included in the polypeptide, and in preferred embodiments, the entire costimulatory factor is encoded. The sequences for polynucleotides encoding costimulatory factors and the functional domains are known, and are described in, for example, Linsley et al. (1990) (human) and Freeman et al., J. Immunol., 143:2714–2722 (1989) (mouse).

The target antigen polypeptide expressed from the recombinant polynucleotide is all or a fragment of a target antigen that is naturally encoded in the pathogenic intracellular microorganism against which an enhanced or augmented immune response is desired, and is comprised of one or more agretopes from that microorganism. Target antigens are preferably from viruses, and particularly viruses that result in chronic infections, for example, the hepadnaviruses (including HBV), the lentiviruses (including HIV), herpesviruses (including HSV-1, HSV-2, EBV, CMV, VZV, and HHV-6), and the flaviviruses/pestiviruses (including HCV). Also included as viruses that cause chronic viral infections are human retroviruses, for example, human T lymphotropic viruses (HTLV-1 and HTLV-2) that cause T cell leukemia and myelopathies. Other organisms that cause chronic infections include, for example, pathogenic protozoa, (e.g., *Pneumocystis carinii*, trypanosoma, malaria and *Toxoplasma gondii*), bacteria (e.g., mycobacteria, salmonella and listeria) and fungi (e.g. candida and aspergillus).

The nucleotide sequences of a number of these viruses, including different species, strains, and isolates are known in the art. For reviews see: Robinson (1990) (Hepadnaviridae); Levy, *Microbiological Reviews*, 57:183–289 (1993) (HIV); and Choo et al., *Seminars in Liver Disease*, 12:279–288 (1992) (HCV). Particularly suitable target antigens are those which induce a T cell response, and particularly a CTL-response during infection. These may include, for example, from HBV, the core antigen, the E antigen, and the surface antigen (HBsAg). Polynucleotide sequences for HBsAg including the pre-S1, pre-S2 and S regions from a variety of surface antigen subtypes are known in the art. See, for example, Okamoto et al., *J. Gen. Virol.*, 67:1383–1389 (1986); Genbank accession numbers D00329 and D00330. The polynucleotide sequences encoding HIV glycoprotein gp160 and other antigenic HIV regions are known in the art. Lautenberger et al., *Nature*, 313:277–284 (1985); Starcich et al., *Cell*, 45:637–648 (1986); Wiley et al., *Proc. Natl. Acad. Sci. USA*, 83:5038–5042 (1986); and Modrow et al., *J. Virol.*, 61:570–578 (1987).

It is within the scope of the invention to include nucleotides encoding two or more target antigen polypeptides that may or may not be fused. The two target antigen polypeptides may be from the same pathogenic intracellular microorganism, or when it is desirable to enhance the immune response to more than one microorganism, from differing microorganisms.

The sequences encoding the costimulatory factor and the target antigen polypeptide are operably linked to a transcriptional control region. Transcriptional control regions are known in the art, and include, for example, regions isolated from the following: the human cytomegalovirus (HCMV) IE94 promoter region (Boshart et al., *Cell*, 41:521–530 (1985)); the human IL-2 gene (Fujita et al., *Cell*, 46:401–407 (1986)); the human IFN-γ gene (Ciccarone et al., *J. Imunol.*, 144:725–730 (1990)); the human IL-3 gene (Shoemaker et al., *Proc. Natl. Acad. Sci. USA*, 87:9650–9654 (1990)); th& human IL-4 gene (Arai et al., *J. Immunol.*, 142:274–282 (1989)); the human lymphotoxin gene (Nedwin et al., *Nucl. Acids. Res.*, 13:6361–6373 (1985)); the human granulocyte-macrophage CSF (GM-CSF) gene (Miyatake et al., *EMBO J.*, 4:2561–2568 (1985)); the human perforin gene (Lictenheld et al., *J. Immunol.*, 143:4267–4274 (1989)); the human 519 gene (Manning et al., *J. Immunol.*, 148:4036–4042 (1992)); the human granzyme B (CTLA-1) gene (Haddad et al., *Gene*, 87:265–271 (1990)); the human CTLA-4 gene (Harper et al., *J. Immunol.*, 147:1397–1044 (1991)); the human CGL-2 gene (Heusel et al., *J. Biol. Chem.*, 266:6152–6158 (1991)); the human granzyme H gene (Haddad et al., *Int. Immunol.*, 3:57–66 (1990)); the human IL-2 receptor, α chain gene (Cross et al., *Cell*, 49:47–56 (1987)); the Murine T cell activation 3 (TCA-3) gene (Wilson et al., *J. Immunol.*, 141:1563–1570 (1988)); and the human CD69 gene.

In some embodiments of the invention, the transcriptional control regions are hybrids. For example, enhancer regions (e.g., from the HCMV IE transcriptional control region and/or from the SV40 early promoter region) may be inserted upstream of the transcriptional control regions. Alternatively, or in addition, multimeric transcription factor binding sites (e.g., NF-AT and/or NFKB) may be inserted into or upstream of the transcriptional control regions, combining the upstream region of one with the proximal region of the other. Secretion signals may also be included where appropriate, whether from a native protein or from other secreted polypeptides of the same or related species, which allow the protein to cross and/or lodge in cell membranes, and thus attain its functional topology, or to be secreted from the cell.

In addition it is useful to include in the recombinant polynucleotides a positive marker that enables the selection of cells carrying the recombinant polynucleotide. The positive selectable-marker my be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the aminoglycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

The sequences encoding the costimulatory factor and the target antigen polypeptide(s) may be on separate polynucleotides, but preferably are on the same polynucleotide. These encoding sequences my also be under the control of separate transcriptional control sequences, or under the control of the same transcriptional control sequence.

In addition to transcriptional control regions, in some embodiments, the polynucleotides encoding the costimulatory factor and target antigen(s) are in the form of recombinant expression vectors.

Techniques for nucleic acid manipulation are described generally, for example, in Sambrook et al. (1989), Ausubel et al. (1987); and in *Annual Reviews of Biochemistry*, 61:131–156 (1992). Reagents useful in applying such techniques, such as restriction enzymes and the like, are widely known in the art and commercially available from a number of vendors.

Large amounts of the polynucleotides used to create the cells of the present invention may be produced by replication in a suitable host cell. The natural or synthetic polynucleotide fragments coding for a desired fragment may be incorporated into recombinant nucleic acid constructs, typically polyucleotide constructs, Capable of introduction into and replication in a prokaryotic or eukaryotic cell. Usually the constructs will be suitable for replication in a unicellular host, such as yeast or bacteria, but may also be intended for introduction to, with and without and integration within the genome, cultured mammalian or plant or other eukaryotic cell lines. The purification of nucleic acids produced by the methods of the present invention are described, e.g., in Sambrook et al. (1989).

The polynucleotides used in the present invention may also be produced in part or in total by chemical synthesis, e.g., by the phosphoramidite method described by Beaucage and Carruthers, *Tetra. Letts.*, 22:1859–1862 (1981) or the triester method according to the method described by Matteucci et al., *J. Am. Chem. Soc.*, 103:3185 (1981), and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host cell for replication will typically comprise a replication system recognized by the host, including the intended recombinant polynucleotide fragment encoding the desired polypeptide. Such vectors may be prepared by means of standard recombinant techniques well known in the art and discussed, for example, in Sambrook et al. (1989) or Ausubel et al. (1987).

Preferably, during the cloning phase, the polynucleotide construct will contain a selectable marker, a gene encoding a protein necessary for the survival or growth of a host cell transformed with the vector. The presence of this gene ensures the growth of only those host cells which express the inserts. Typical selection genes encode proteins that (a) confer resistance to antibiotics or other toxic substances, e.g. ampicillin, neomycin, methotrexate, etc.; (b) complement auxotrophic deficiencies, or (c) supply critical nutrients not available from complex media, e.g. the gene encoding D-alanine racemase for Bacilli. The choice of the proper selectable marker will depend on the host cell, and appropriate markers for different hosts are well known in the art.

The recombinant polynucleotides encoding the costimulatory factor and target antigen polypeptide may be introduced into individuals in several ways. For example, the polynucleotides may be introduced ex vivo into a host cell, for example, dendritic cells, or cells from a skin biopsy. The cells containing the recombinant polynucleotide may be used to confer immunity to individuals. The cells are usually administered by infusion, with each infusion in a range of at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician or veterinarian, and can be determined by routine examination.

The polynucleotides encoding the costimulatory factor and the target antigen polypeptide may be introduced into the desired cell ex vivo by means known in the art, including, for example/transformation, electroporation, lipofection, and transduction, including the use of adeno-associated viral (AAV) vectors, and particularly using methods of retroviral gene transfer known in the art.

Various infection techniques have been developed which utilize recombinant infectious virus particles for gene delivery. This represents a preferred approach to the present invention. The viral vectors which have been used in this way include virus vectors derived from simian virus 40 (SV40; Karlsson et al., *Proc. Natl. Acad. Sci. USA*, 82:158 (1985)), adenoviruses (Karlsson et al., *EMBO J.*, 5:2377 (1986)), AAV (Carter, Current Opinion in Biotechnology 1992, 3:533–539), and retroviruses (Coffin, in Weiss et al. (eds.), RNA Tumor Viruses, 2nd ed., Vol. 2, Cold Spring Harbor Laboratory, New York, 1985, pp. 17–71). Thus, gene transfer and expression methods are numerous but essentially function to introduce and express genetic material in mammalian cells. Several of the above techniques have been used to transduce hematopoietic or lymphoid cells, including calcium phosphate transfection (Berman et al. (1984)), protoplast fusion (Deans et al. (1984)), electroporation (Cann et al., *Oncogene*, 3:123 (1988)), and infection with recombinant adenovirus (Karlsson et al. (1986)); Reuther et al., *Mol. Cell. Biol.*, 6:123 (1986); AAV (Carter (1985)) and retrovirus vectors (Overell et al., *Oncogene* 4:1425 (1989)).

Retroviral vectors provide a highly efficient method for gene transfer into eukaryotic cells which is the preferred method for the delivery of the polynucleotides of the invention. Moreover, retroviral integration takes place in a controlled fashion and results in the stable integration of one or a few copies of the new genetic information per cell.

Retroviruses are a class of viruses which replicate using a virus-encoded, RNA-directed DNA polymerase, or reverse transcriptase, to replicate a viral RNA genome to provide a double-stranded DNA intermediate which is incorporated into chromosomal DNA of an arian or mammalian host cell. Most retroviral vectors are derived from murine retroviruses. Retroviruses adaptable for use in accordance with the present invention can, however, be derived from any avian or mammalian cell source. These retroviruses are preferably amphotropic, meaning that they are capable of infecting host cells of a broad host range of several species, including humans.

A characteristic feature of retroviral genomes (and retroviral vectors used as described herein) is the retroviral long terminal repeat, or LTR, which is an untranslated region of about 600 base pairs found in slightly variant forms at the 5' and 3' ends of the retroviral genome. When incorporated into DNA as a provirus, the retroviral LTR includes a short direct repeat sequence at each end and signals for initiation of transcription by RNA polymerase II and 3' cleavage and polyadenylation of RNA transcripts. The LTR contains all other cis-acting sequences necessary for viral replication.

A "provirus" refers to the DNA reverse transcript of a retrovirus which is stably integrated into chromosomal DNA in a suitable host cell, or a cloned copy thereof, or a cloned copy of unintegrated intermediate forms of retroviral DNA. Forward transcription of the provirus and assembly into infectious virus occurs in the presence of an appropriate helper virus or in a cell line containing appropriate sequences enabling encapsidation without coincident production of a contaminating helper virus. Mann et al., describe the development of "packaging" cell lines (e.g., ψ2) which can be used to produce helper-free stocks of recombinant retrovirus. *Cell*, 3:153 (1983).

Packaging cell lines contain integrated retroviral genomes which lack sequences required in cis for encapsidation, but which provide all necessary gene product in trans to produce intact virions. The RNA transcribed from the integrated mutant provirus cannot itself be packaged, but these cells can encapsidate RNA transcribed from a recombinant retrovirus introduced into the same cell. The resulting virus particles are infectious, but replication-defective, rendering them useful vectors which are unable to produce infectious virus following introduction into a cell lacking the complementary genetic information enabling encapsidation.

Encapsidation in a cell line harboring transacting elements encoding an ecotropic viral envelope (e.g., ψ2) provides ecotropic (limited host range) progeny virus. Alternatively, assembly in a cell line containing amphotropic packaging genes (.e.g., PA317, ATCC CRL 9078) provides amphotropic progeny virus. Miller and Buttimore, *Mol. Cell. Biol.,* 6:2895 (1986). Such packaging cell lines provide the necessary retroviral gag, pol and env proteins in trans. This strategy results in the production of retroviral particles which are highly infectious for mammalian cells, while being incapable of further replication after they have integrated into the genome of the target cell. The product of the env gene is responsible for the binding of the retrovirus to viral receptors on the surface of the target cell and therefore determines the host range of the retrovirus. The PA317 cells produce retroviral particles with an amphotropic envelope protein, which can transduce cells of human and other species origin. Other packaging cell lines produce particles With ecotropic envelope proteins, which are able to transduce only mouse and rat cells.

Numerous retroviral vector constructs have been used successfully to express many foreign genes (see, e.g., Coffin (1985). Retroviral vectors with inserted sequences are generally functional, and few sequences that are consistently inhibitory for retroviral infection have been identified. Functional polyadenylation motifs inhibit retroviral replication by blocking retroviral RNA synthesis, and there is an upper size limit of approximately 11 kb of sequence which can be packaged into retroviral particles; however, the presence of multiple internal promoters, initially thought to be problematic, was found to be well tolerated in several retroviral constructs. Coffin (1985); and Overell et al., *Mol. Cell. Biol.,* 8:1803 (1983).

Many gene products have been expressed in retroviral vectors. This can either be achieved by placing the sequences to be expressed under the transcriptional control of the promoter incorporated in the retroviral LTR, or by placing them under the control of a heterologous promoter inserted between the LTRs. The latter strategy provides a way of coexpressing a dominant selectable marker gene in the vector, thus allowing selection of cells which are expressing specific vector sequences.

In other embodiments of the invention, the recombinant polynucleotides encoding the costimulatory factor and target antigen polypeptide are introduced directly into the individual to be treated and/or immunized. In one embodiment the polynucleotides of the invention are administered directly to the individual to be treated. In this method it is preferred that the polynucleotide encode both the costimulatory factor and the target antigen polypeptide. In addition, it is preferred that the polynucleotide be in the form of an expression vector.

The polynucleotides are mixed with suitable excipients, and administered to the individual by any suitable means known in the art, including, for example parenteral (including, for example, intravenous, intraperitoneal, intramuscular, and subcutaneous) ingestion, lipofection, and transdermal. Suitable excipients are known in the art, and my be dependent upon the species of the individual to which the polynucleotides are administered as well as the mode of administration. The amount of polynucleotide to be administered to the individual is an amount sufficient to render immunity to the immunized individual. This amount will vary depending upon the individual treated, and will be determined by the physician or veterinarian rendering the treatment. The amount to be administered as well as the time of administration (prior to or post-infection) and the number of doses whether single or multiple, is determined by routine methods known to those of skill in the art.

In another embodiment of the invention, the polynucleotides of the invention are encapsidated in virions, and the individual is treated with the encapsidated polynucleotide. The virions used my be any of those that are known in the art to be suitable for gene therapy procedures, several of which are discussed above for the introduction of the polynucleotides into a cell ex vivo. The mode of administration is dependent upon the virion used, and my include, for example, those listed above for administration of unencapsidated polynucleotides. The virions are prepared in a suitable excipient, and administered to the individual. The amount to be administered as well as the time of administration (prior to or post-infection) and the number of doses whether single or multiple, is determined by the administering physician or veterinarian, and is obtainable by routine methods known to those of skill in the art.

The examples presented below are provided as a further guide to the practitioner of ordinary skill in the art, and are not to be construed as limiting the invention in any way.

EXAMPLE 1

Design of an Expression Vector Encoding a B7 Polypeptide and GSVH c-polypeptide as a Viral Target-Antigen Polypeptide Chronic ground squirrel hepatitis virus (GSVH) infection of Beechey ground squirrels is a model system for HBV infection in humans. (Cf. Seeger et al., *J. Virol.,* 51:367–375 (1984)). The present example describes a retroviral vector construct for expression of the B7 gene and a gene encoding the c-antigen (cAg) of GSVH.

The vector construct utilizes the Moloney murine leukemia virus (MMLV) based replication-incompetent vector pMV-7 (Ausubel et al. (1989); and Kirschmeier et al., *DNA,* 2:219–225 (1988)). pMV-7 contains a neomycin resistant gene under the control of the HSV thymidine kinase (TK) promoter, thus allowing selection in tissue culture of cells containing the vector.

The GSHV c-gene including the precore sequence is used as a polynucleotide sequence encoding a target antigen. The GSVH c-gene is isolated from the viral genome (EMBC/Genbank Accession Number K02715) by polymerase chain reaction (PCR). Marion et al., *Proc. Natl. Acad. Sci. USA,* 77.:2941–2945 (1980) and Seeger. (1984). The isolated. GSHV c-gene is then introduced into the pMV-7 vector under Control of the MMLV LTR.

Human B7 cDNA (EMBL/Genbank Accession Number M27533) is cloned as cDNA amplified by PCR from the B7 mRNA of the Raji human B cell line using primers designed from the published cDNA sequence. Freeman (1989). cDNA encoding the B7-1 gene was introduced into the same vector as the GSVH c-gene under control by the CMV immediate early promoter. Gaballe et al., *J. Virol.,* 62:3334–3340 (1988).

The pMV-7 based vector construct encoding the B7 polypeptide and cAg polypeptide was transfected into a retroviral packaging cell line, psi-2. Miller et al., *Mol. Cell. Biol..,* 6:2895–2902 (1986). The transfected cells are then selected by growing in a culture medium containing neomycin. Replication-incompetent retrovirus with an amphotropic envelope produced by the cells grown in the neomycin culture were found in the culture medium.

EXAMPLE 2

Design of an Expression Vector Encoding a B7 polypeptide and GSVH GSHsAg-polypeptide as a Viral Target-Antigen Polypeptide The construct is prepared as in Example 1, except that the GSVH polynucleotide encoding ground squirrel hepatitis surface antigen (GSHsAg) including the pre-S1, pre-S2 and S regions is substituted for that encoding GSVH cAg. The polynucleotide sequence encoding the aforementioned S regions is described in Seeger et al. (1984).

EXAMPLE 3

Use of a Vector Encoding B7 Polypeptide and GSHsAg to Confer Immunity to Uninfected Individuals to GSHV A therapeutically effective amount of a composition comprised of an infectious retroviral vector packaged in an amphotropic envelope ($10^7$ tissue culture infectious units) containing polynucleotide sequences encoding a B7 polypeptide and a GSHsAg polypeptide is administered parenterally to an uninfected and GSHV susceptible Beechey ground squirrel. Seeger et al. (1984). The vector is of the construction described in Example 2. An "uninfected" GSHV susceptible ground squirrel has no detectable serum antibody to ground squirrel hepatitis virus core antigen (anti-GSHcAg) or antibody to ground squirrel hepatitis virus surface antigen (anti-GSHsAg). The parenteral administration of a retroviral vector containing the B7 gene and GSHV gene results in a serum anti-GSHsAg response and a CTL response directed at cells expressing GSHsAg.

The dual response, i.e., serum and CTL, confers at least partial immunity against future infection by GSHV on the uninfected ground squirrel.

EXAMPLE 4

Use of A Vector Encoding B7 Polypeptide and GSHsAg Polypeptide for Treatment of Chronic Virus Infection Two different methods my be used to administer polynucleotides encoding a B7 polypeptide and a viral target antigen to animals chronically infected with GSHV for treatment of an infection.

Delivery of the Vector Encoding the B7 polypeptide and GSHsAg Polypeptide Directly to an Infected Mammal An infectious retroviral vector packaged in an amphotropic envelope and encoding a B7 polypeptide and a GSHcAg polypeptide are constructed as in Example 1. The vector is administered parenterally in a therapeutically effective amount to a ground squirrel chronically infected with GSHV.

The effect of the expression of polypeptides from the retroviral vector on the immune response by the ground squirrel, including a CTL response directed at cells expressing GSHcAg, is monitored. In addition, the effect on the chronicity of the disease, including the presence of viral DNA, the presence of GSHsAg and pathogenic effects associated with the disease is monitored. Diminution in physical symptomology and/or in GSHsAg and/or in GVSH DNA in the treated individual is indicative of alleviation and/or termination of the chronic disease caused by GSHV.

Treatment of an Infected Mammal with Cells Transfected ex vivo with a Vector Encoding B7 Polypeptide and GSH cAg Fibroblast cells isolated from a skin biopsy of the infected individual are grown in culture, and are transfected with a retroviral vector encoding a B7 polypeptide and a GSHcAg polypeptide. The vector is constructed as described in Example 1. Infected (transduced) cells are then selected by growing cells in a culture medium containing neomycin. The cells expressing GSHcAg are identified by using fluorescent staining (IFA) with anti-HBc and B7 protein expression using ELISA with anti-B7 monoclonal antibody (mAb). A therapeutically effective amount of the autologous cells expressing GSHcAg and B7 are infused intravenously into the GSHV infected ground squirrel.

The effect of the expression of polypeptides from the retroviral vectors in the-implanted cells on the immune response by the ground squirrel, including a CTL response directed at cells expressing GSHcAg, is monitored. In addition, the effect on the chronicity of the disease, including the presence of viral DNA, the presence of GSHsAg and pathogenic effects associated with the disease is monitored. Diminution in physical symptomology and/or in GSHsAg and/or in GVSH DNA in the treated individual is indicative of alleviation and/or termination of the chronic disease caused by GSHV.

EXAMPLE 5

Construction of retroviral vectors to express B7 and HBS

FIG. 1 depicts recombinant retroviral vectors for the demonstration of the enhancement of the immune response to hepatitis B virus surface antigen (HBS) by co-expression with B7-1 in cells in vivo. Retroviral vector pMV-7 DNA was used to construct recombinant vectors 907 with the HBS coding sequence inserted at the polylinker of pMV-7 ; and recombinant vector 1016 with the HBS coding sequence, a cap independent translation element (CITE) of encephalomycoarditis virus (EMC) and the coding sequence for murine B7-1 all in the same reading frame inserted at the polylinker of pMV-7. Each recombinant vector was used to transfect by the calcium phosphate DNA method a murine Balbc packaging cell line and cells containing the respective vectors were selected by growth in cell culture medium containing neomycin. The packaging cell population neomycin selected to contain recombinant vector 907 and those selected for recombinant vector 1016 released virus that could be assayed by the ability to confer neomycin resistance to Balbc 3T3 cells. Neomycin resistant Balbc 3T3 cells infected with recombinant virus 907 were shown to release HBS by ELISA. Neomycin resistant Balbc 3T3 cells infected with recombinant virus 1016 were shown to express HBS as above and the B7-1 protein by FACS analysis using monoclonal antibody to the B7-1 protein. Cells ($2 \times 10^7$) of each respective type and nontransfected Balbc 3T3 cells were each inoculated into seperate groups of 10 Balbc mice by the intrapertioneal route for study of the immune response to HBS. Anti-HBS measured by ELISA, proliferation of spleen cells exposed to HBS in vitro and cytotoxic activity of spleen cells by chromium 51release from Balbc 3T3 cells expressing HBS are assayed in 5 mice of each group at 2 weeks and 5 mice of each group at 4 weeks post inoculation. In FIG. 1, LTR represents the long terminal repeats of the retroviral vector, TK represents the thymidine kinase promoter of herpes simplex virus, Neo represents a gene conferring neomycin resistance.

Although the foregoing invention has been described in some detail byway of illustration and example for purposes of clarity and understanding, it will be apparent to those skilled in the art that certain changes and modifications may be practiced. Therefore, the description and examples should not be construed as limiting the scope of the invention which is delineated by the appended claims.

What is claimed:

1. A method of enhancing an antigen-specific T cell response in an individual to a target antigen comprising administering at least one polynucleotide sequence encoding at least one target antigen or a portion of the target antigen and at least one polynucleotide sequence encoding at least one B7 costimulatory molecule that interacts with T cell surface molecules for T cell activation, said polynucleotide sequences expressed in an amount effective to enhance a T cell response to eliminate cells bearing said target antigen or portion thereof, when said polynucleotide sequence encoding the target antigen and said polynucleotide sequence encoding the B7 costimulatory molecule are expressed in said individual.

2. The method according to claim 1, wherein said B7 costimulatory molecule is selected from the group consisting of B7-1, B7-2 and B7-3 molecules.

3. The method of claim 1 wherein said target antigen is an antigen of an infectious agent.

4. The method of claim 3 wherein said infectious agent is selected from the group consisting of viruses, protozoans, fungi, bacteria, parasites and worms.

5. The method of claim 1 wherein said polynucleotide sequence encoding the target antigen or a portion of the target antigen is operably linked to a transcriptional control region in a vector.

6. The method of claim 1 wherein said polynucleotide sequence encoding the B7 costimulatory molecule is operably linked to a transcriptional control region in a vector.

7. The method of claim 1 wherein said polynucleotide sequence encoding the target antigen or a portion of the target antigen is operably linked to a transcriptional control region in a vector and said polynucleotide sequence encoding the B7 costimulatory molecule is operably linked to a transcriptional control region in said vector.

8. The method according to claim 5, 6 or 7 wherein said vector is a vital vector.

9. The method of claim 5, 6 or 7 wherein said vector is a polynucleotide vector.

10. A vector comprising at least one polynucleotide sequence encoding at least one target antigen or encoding a portion of said target antigen and at least one polynucleotide sequence encoding at least one B7 costimulatory molecule that interacts with T cell surface molecules for T cell activation when said B7 costimulatory molecule and said antigen are both expressed in an individual, wherein said polynucleotide sequences are expressed in an amount effective to enhance the T cell response to eliminate cells bearing said target antigen or portion thereof, and wherein said polynucleotide sequence encoding the target antigen is operably linked to a transcriptional control region and said polynucleotide sequence encoding the B7 costimulatory molecule is operably linked to a transcriptional control region for expression in said individual.

11. The vector of claim 10, wherein said B7 costimulatory molecule is selected from the group consisting of B7-1, B7-2 and B7-3 molecules.

12. The vector of claim 10 wherein said vector is a viral vector.

13. The vector of claim 10 wherein said vector is a polynucleotide vector.

14. The vector of claim 10 wherein said target antigen is an antigen of an infectious agent.

15. The vector of claim 14 wherein said infectious agent is selected from the group consisting of viruses, protozoans, fungi, bacteria, parasites and worms.

* * * * *

UNITED STATES PATENT AND TRADEMARK OFFICE
CERTIFICATE OF CORRECTION

PATENT NO. : 5,738,852
DATED : April 14, 1998
INVENTOR(S) : Robinson et al.

It is certified that error appears in the above-identified patent and that said Letters Patent is hereby corrected as shown below:

[73] Assignee: should read --Solis Terapeutics, Inc. Pala Alto, Calif.; and

Leland Stanford Junior University, Palo Alto,

Calif.--

Signed and Sealed this

Twelfth Day of June, 2001

*Attest:*

*Attesting Officer*

NICHOLAS P. GODICI
*Acting Director of the United States Patent and Trademark Office*